United States Patent [19]
Friese et al.

[11] Patent Number: 6,164,120
[45] Date of Patent: Dec. 26, 2000

[54] DETECTOR AND METHOD FOR THE PRODUCTION THEREOF

[75] Inventors: Karl-Hermann Friese; Heinz Geier, both of Leonberg; Helmut Weyl, Schwieberdingen; Hans-Martin Wiedenmann, Stuttgart, all of Germany

[73] Assignee: Robert Bosch GmbH, Stuttgart, Germany

[21] Appl. No.: 09/171,688

[22] PCT Filed: Dec. 16, 1997

[86] PCT No.: PCT/DE97/02916

§ 371 Date: Feb. 22, 1999

§ 102(e) Date: Feb. 22, 1999

[87] PCT Pub. No.: WO98/38500

PCT Pub. Date: Sep. 3, 1998

[30] Foreign Application Priority Data

Feb. 25, 1997 [DE] Germany ............................ 197 07 458

[51] Int. Cl.[7] .................................................. G01N 27/407
[52] U.S. Cl. ........................ 73/23.2; 73/23.31; 73/31.05; 204/424; 204/426
[58] Field of Search ................................ 73/23.31, 23.32, 73/31.05, 23.2; 204/424, 426; 338/34, 229

[56] References Cited

U.S. PATENT DOCUMENTS

| | | |
|---|---|---|
| 3,920,172 | 11/1975 | Rhee . |
| 4,117,968 | 10/1978 | Naidich et al. ........................ 228/124.1 |
| 4,130,797 | 12/1978 | Hattori et al. ....................... 73/31.05 X |
| 4,189,355 | 2/1980 | Fujishiro et al. .................... 204/426 X |
| 4,310,401 | 1/1982 | Stahl ......................................... 204/426 |
| 4,334,974 | 6/1982 | Muller et al. ............................ 204/426 |
| 4,818,363 | 4/1989 | Bayha et al. ............................. 204/426 |
| 5,290,421 | 3/1994 | Reynolds et al. . |
| 5,329,806 | 7/1994 | McClanahan et al. ................. 73/31.05 |
| 5,377,899 | 1/1995 | Hashimoto ............................... 228/117 |
| 5,533,258 | 7/1996 | Rainer et al. ......................... 29/890.03 |
| 5,795,454 | 8/1998 | Friese et al. ............................. 204/424 |
| 5,846,391 | 12/1998 | Friese et al. ............................. 204/424 |
| 5,942,092 | 8/1999 | Weyl et al. .............................. 204/424 |
| 6,083,371 | 7/2000 | Weyl et al. .............................. 204/426 |

FOREIGN PATENT DOCUMENTS 195 23 903  1/1997  Germany .

*Primary Examiner*—Daniel S. Larkin
*Attorney, Agent, or Firm*—Kenyon & Kenyon

[57] ABSTRACT

A sensor for determining an oxygen level in an exhaust gas of an internal combustion engine includes a receptacle arranged in a longitudinal bore of a metallic enclosure for a sensor element. The sensor element is accommodated in a gas-tight manner using a sensor element seal. The receptacle has a measured gas-side ceramic molded component and a connection-side ceramic molded component, which are arranged one behind the other axially. A hollow space is formed between the measured gas-side ceramic molded component and the connection-side ceramic molded component, in which a metallic sealing element is hot-pressed.

13 Claims, 4 Drawing Sheets

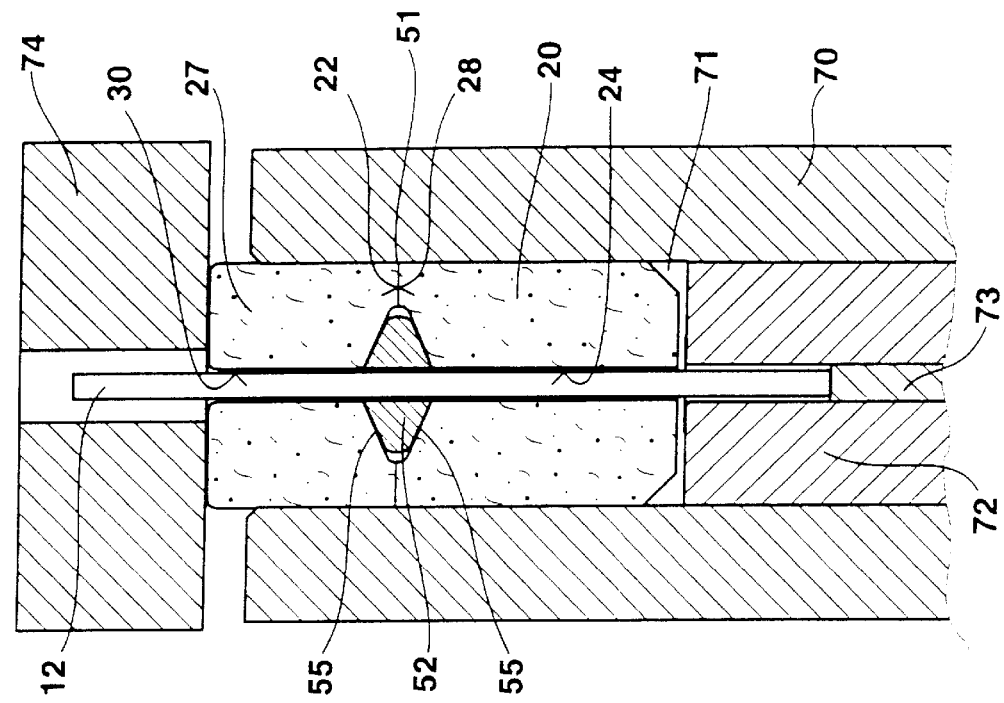
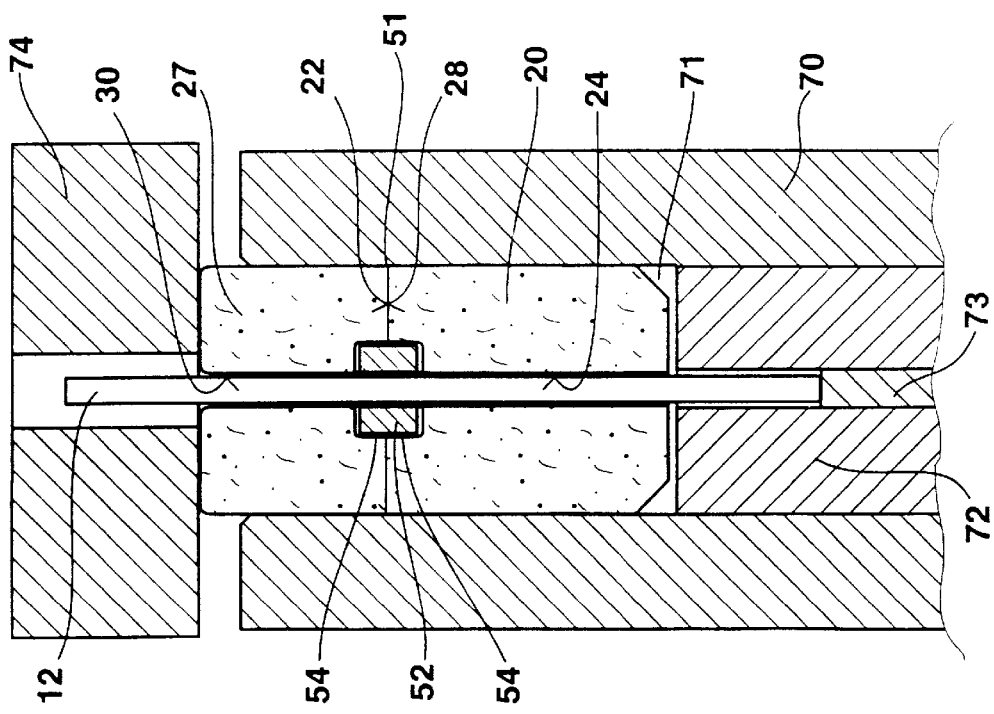

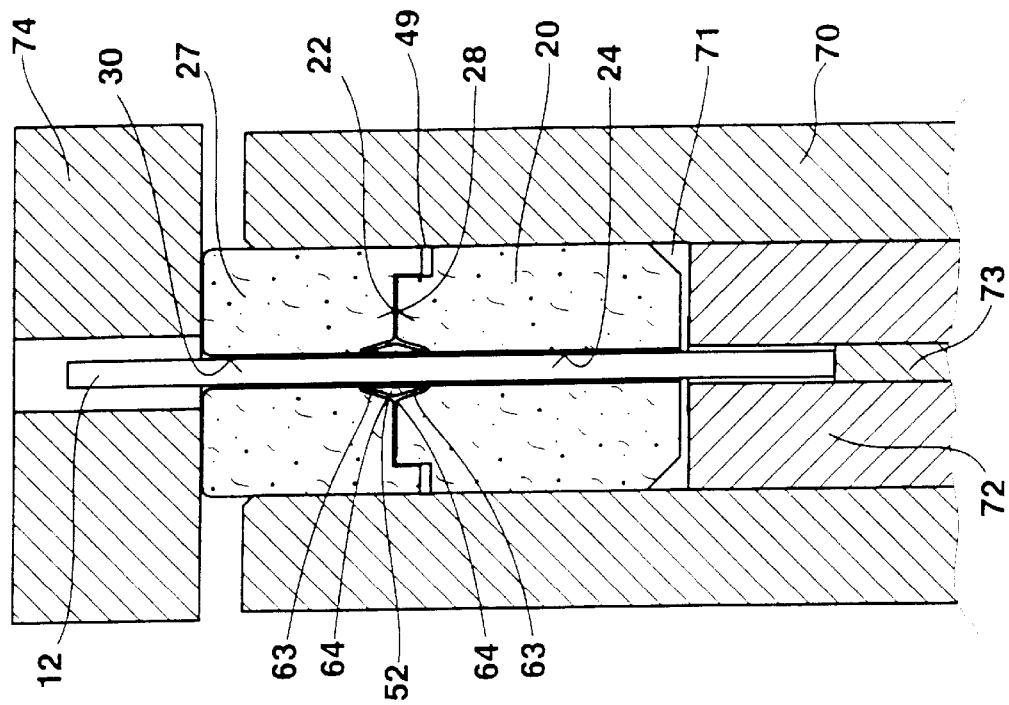
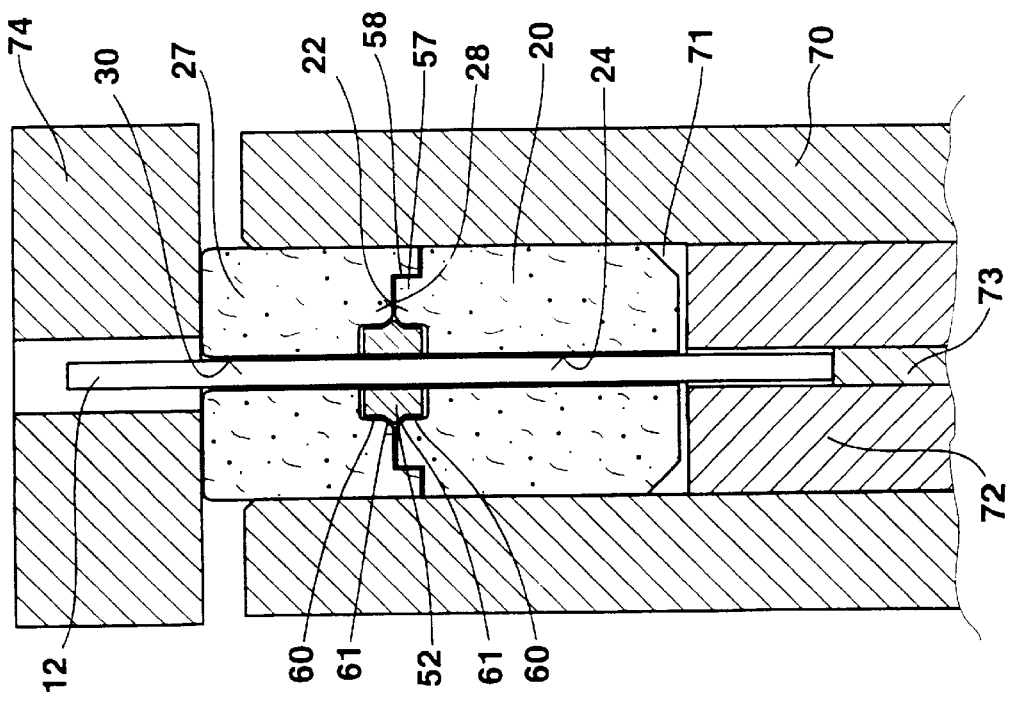

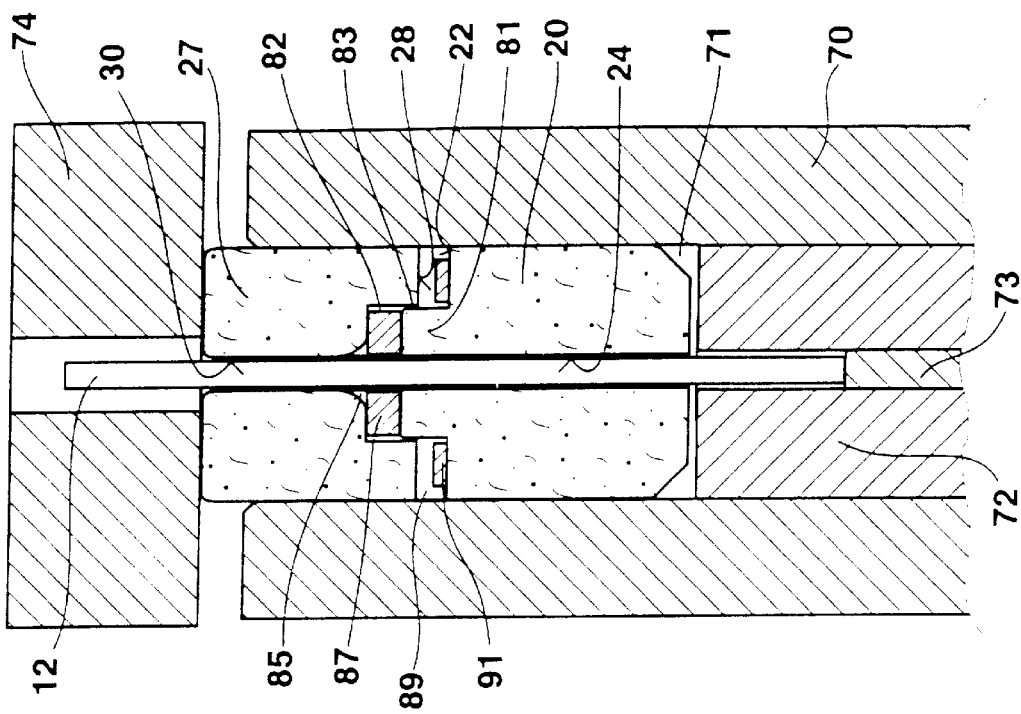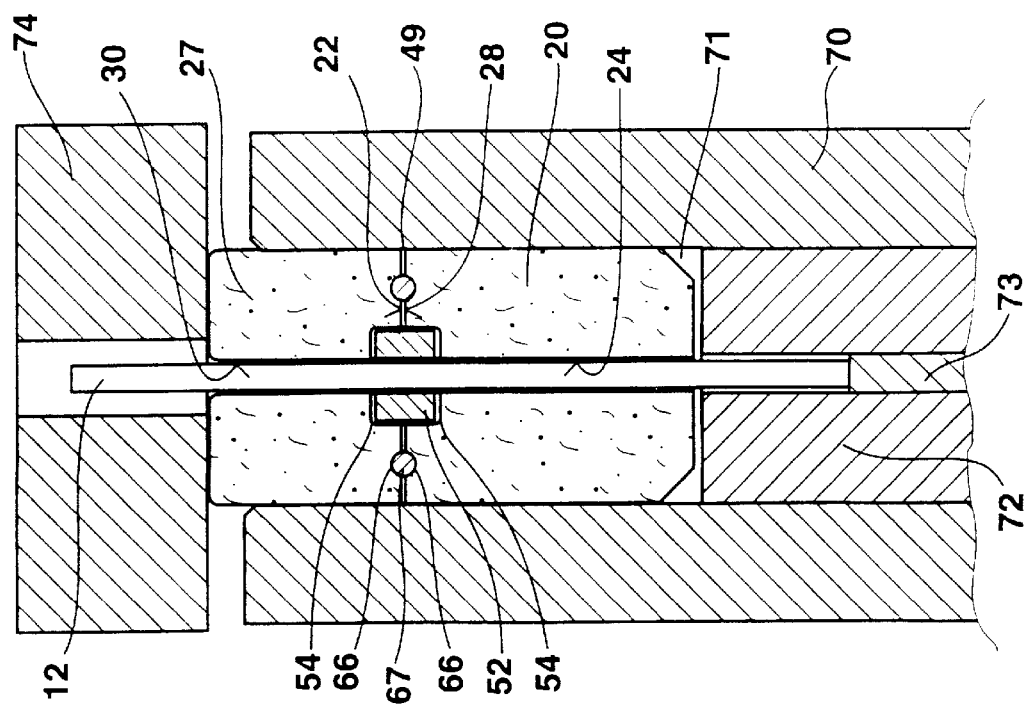

DETECTOR AND METHOD FOR THE PRODUCTION THEREOF

BACKGROUND INFORMATION

The present invention relates to a sensor and a method of manufacturing a sensor. in which German published patent application No. 19523903 describes a known sensor a planar sensor element is secured, in a gas-tight manner, in a bushing of an exhaust gas-side ceramic molded component, using metal solder. The exhaust gas-side ceramic molded component has a depression on its end facing away from the exhaust gas, in which the metal solder is introduced.

SUMMARY OF THE INVENTION

The sensor according to the present invention has the advantage that a mechanically more stable and more gas-tight bond between the planar sensor element and the ceramic molded component can be achieved. The ductile metal-based sealing element ensures sufficient protection against crack formation in the area of the join. Hot forming of the metal-based sealing element allows a combination joining method to be used, in which the process operations of hot forming, shrink-fitting, and optionally diffusion welding are combined. The method according to the present invention allows the sensor element seal to be manufactured in a cost-effective manner. In the joining process, the sealing element is hot-formed between the two ceramic molded components so that the planar sensor element is enclosed and the sealing element is sealingly pressed against the surface of the sensor element.

According to the present invention it is particularly advantageous if the formable sealing element and the geometry of the hollow space or gap between the two ceramic molded components are designed so that the material of the sealing element can expand on the sensor element within certain limits, even axially, during hot forming. The joining process is advantageously performed above the maximum temperatures of use occurring later, so that the sealing element is shrink-fitted onto the sensor element due to its; higher thermal expansion coefficient and possibly additional diffusion welding can take place between the sealing element, the sensor element and the ceramic molded component.

BRIEF DESCRIPTION OF THE DRAWINGS

FIG. 2 shows a first embodiment of a sensor element seal with a device for manufacturing the seal according to the present invention.

FIG. 3 shows another embodiment of the sensor element seal of FIG. 2.

FIG. 4 shows yet another embodiment of the sensor element seal of FIG. 2.

FIG. 5 shows still another embodiment of the sensor element seal of FIG. 2.

FIG. 6 shows still another embodiment of the sensor element seal of FIG. 2.

FIG. 7 shows yet another embodiment of the sensor element seal of FIG. 2.

DETAILED DESCRIPTION

Figure 1:
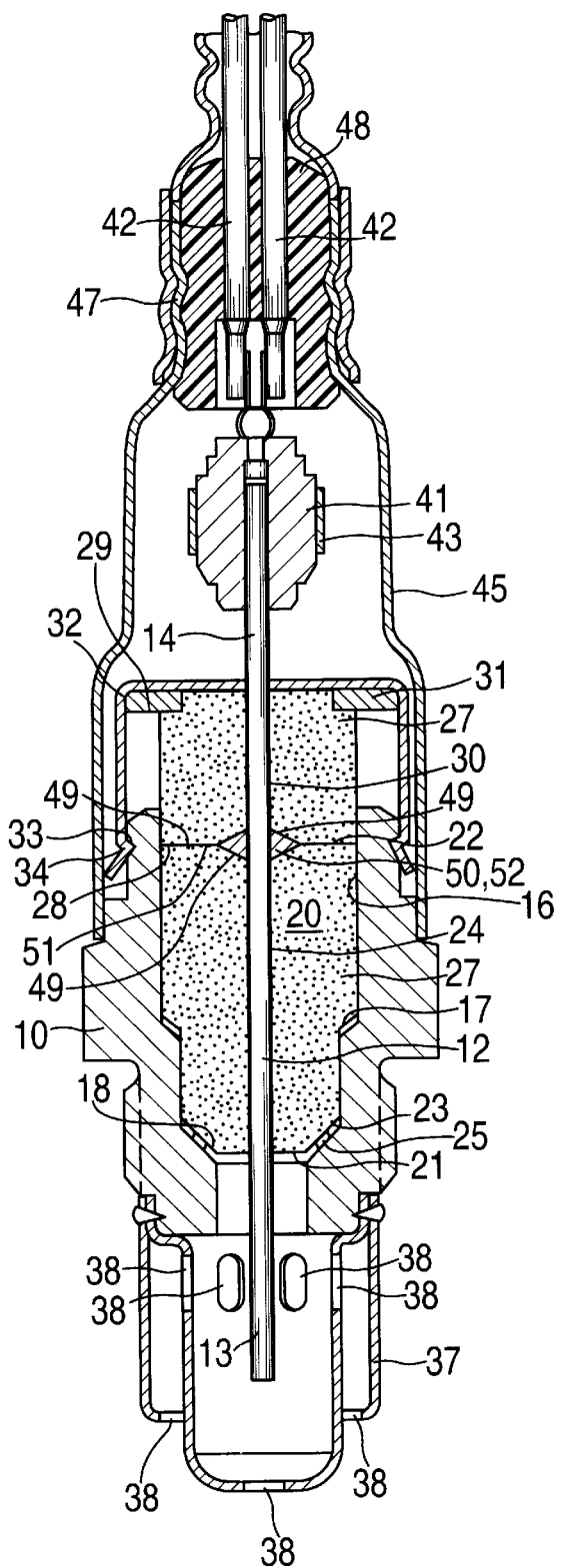
FIG. 1 shows a cross-section through the sensor according to the present invention.

The sensor illustrated in FIG. 1 is an electrochemical sensor for determining the oxygen level in exhaust gases of internal combustion engines. The sensor has a metallic enclosure 10, in which a plate-shaped sensor element 12 is arranged with an end section 13 on the measured gas side, and an end section 14 on the connection side. Enclosure 10 is designed to be installed in an exhaust pipe (not illustrated) using a thread as fastening means. Furthermore, a longitudinal bore 16, with a first shoulder-shaped ring surface 17, for example, and a second shoulder-shaped ring surface 18, is arranged in enclosure 10.

A measured gas-side ceramic molded component 20 is arranged in longitudinal bore 16 with a measured gas-side bushing 24, a measured gas-side face 21, and a connection-side face 22. Measured gas-side face 21 has a conical sealing seat 23, which sits on metallic seal ring 25 in contact with second shoulder-shaped ring surface 18. A connection-side ceramic molded component 27 includes a connection-side bushing 30, with a measured gas-side face 28 and a connection-side face 29 is arranged over measured gas-side ceramic molded component 20.

A mechanically pre-stressed disk spring 31, exerting pressure via a tube-shaped holding cap 32 on connection-side ceramic molded component 27 projecting from enclosure 10, is on connection-side face 29 of connection-side ceramic molded component 27. Holding cap 32 is engaged via catches 34, with annular groove 33 arranged on the outside of enclosure 10. The two ceramic molded components 20, 27 are pre-stressed in the axial direction between holding cap 32 and disk spring 31, so that measured gas-side ceramic molded component 20 presses on seal ring 25 with conical sealing seat 23. Thus, a gas-tight sealing seat is formed between enclosure 10 and ceramic molded component 20.

Measured gas-side end section 13, projecting from the enclosure 10, is surrounded, with a gap, by a double-walled protective tube 37, for example, with gas inlet and gas outlet openings 38. On connection-side end section 14, sensor element 12 has contacts (not illustrated in detail), contacted by a contact plug 41 having connecting cables 42. Contact plug 41 contains, for example, two ceramic components, which are held together by a tension piece 43. Connection-side end section 14, projecting from connection-side ceramic molded component 27, of sensor element 12, is surrounded by a metal sleeve 45, which is welded, in a gas-tight manner, to enclosure 10 and has a tube-shaped opening 47, in which there is a cable bushing 48 for the passage of connecting cables 42.

On faces 22, 28, each of the two ceramic molded components 20, 27 has a depression 49 surrounding bushings 24, 30, so that a hollow space 50 surrounding sensor element 12 is formed when the assembly is mounted together. In the embodiment of FIG. 1, depressions 49 are applied so that they run in a truncated conical shape on both faces 22, 28. In hollow space 50 formed by depressions 49, a seal element 52 is inserted, which tightly surrounds sensor element 12. Furthermore, an annular gap 51 exists between faces 22, 28 of the two ceramic molded components 20, 27. In order to avoid pressure peaks and ensure the smallest possible annular gap 51, faces 22, 28 are advantageously polished.

Sealing element 52 is a hot-formable metal, which is used in the form of a hot-formable compact metal component, or in the form of a metal powder pressed component, or a porous or solid sintered component, or in the form of a metallic foil, or in the form of a cast foil manufactured with an organic binding agent and filled with metal powder.

Copper, aluminum, palladium, nickel, silver, or an alloy of these materials, for example as a metal solder (hard solder, active solder), such as Cu/Ag, Cu/Ag/Ti, Cu/Al, or Al/Si solder, heated to their softening points, are advantageously suitable materials for sealing element 52. Additives can be advantageously added to the materials of sealing element 52. Graphite, boron nitride, talcum, bentonite, kaolin, $MoS_2$, glass, or a mixture of these materials can be used as plasticizers in hot-forming sealing element 52. Copper or aluminum, for example, preferably as in the form of flakes, can be added to the cast foils. The metal powder and graphite also act as reduction agents ($O_2$ getters). However, thermal soot or organic binders are also suitable reduction agents.

The sealing element 52 can, however, also be a composite made of a core with a single-sided or double-sided surface coating. Materials such as copper, nickel, palladium, or an alloy of these materials are well-suited as a core. Aluminum, nickel, palladium, copper, or an alloy of these materials are well-suited as a coating. The coating can be applied by roll-plating and/or surface coating procedures such as electroplating, onto the core. It is, however, a prerequisite that the sealing element 52 in the composite be heated to its softening point so that it can be hot-formed.

Other embodiments of the sensor according to the present invention with a device for manufacturing the sensor element seal are illustrated in FIGS. 2 through 7. The device has a matrix 70 with a receptacle 71, a support die 72, and a securing die 73, as well as a press die 74. Ceramic molded components 20, 27 with sensor element 12 inserted in bushings 24, 30, are positioned in receptacle 71. The axial position of sensor element 12 is defined by securing die 73, sensor element 12 being in contact, with its measured gas-side end section, with securing die 73.

In the embodiment depicted in FIG. 2 on face 22 of measured gas-side ceramic molded component 20 and face 28 of connection-side ceramic molded component 27, there are disk-shaped depressions 54 surrounding bushings 24, 30. Sealing element 52 is pressed into disk-shaped depression 54.

According to the embodiment illustrated in FIG. 3, a conical depression 55 around bushings 24, 30 is formed on both faces 22, 28 with a truncated cone shape, for example, as in the embodiment of FIG. 1. A hot-formable seal ring is pressed in conical depression 55 as sealing element 52.

A fourth embodiment is shown in FIG. 4, where both ceramic molded components 20, 27 have a stepped design, with the measured gas-side ceramic molded component 20 having a die-shaped attachment 57 and the connection-side ceramic molded component 27 having a matrix-shaped depression 58. Bushings 24, 30 are surrounded by disk-shaped depressions 60 on faces 22, 28 of both ceramic molded components 20, 27, and the depressions 60 have a bevel 61 at their edges. Bevels 61 cause the hot-formed sealing element 52 to be pressed more strongly in the direction of sensor element 12 when the two ceramic molded components 20, 27 are pressed together.

FIG. 5 shows a fifth embodiment for forming sealing element 52. The faces 22,28 of the two ceramic molded components 20, 27 have a design similar to that of the embodiment according to FIG. 4, but the orifices of bushings 24, 30 are provided with a conical widening 63 at faces 22, 28, which has a rounding 64 at the edges with the respective face. This embodiment ensures that, when sealing element 52 is hot-formed, it is pressed both in the direction of sensor element 12 and in the direction of annular gap 51.

A sixth embodiment is illustrated in FIG. 6, where, in addition to the design of sealing element 52 according to FIG. 2, both faces 22, 28 of each of ceramic molded components 20, 27 are provided with a circumferential groove 66. An additional sealing element 67 is placed in groove 66. The additional sealing element 67 provides annular gap 51 with additional sealing.

Another embodiment is illustrated in FIG. 7, where measured gas-side ceramic molded component 20 has a die-shaped attachment 81 on its connection-side face 22. Connection-side ceramic molded component 27 has on its measured gas-side face 28 a matrix-shaped depression 82, into which die-shaped attachment 81 is inserted with a radial gap 83. A hollow space 85 is formed between the face of die-shaped attachment 81 and the bottom of matrix-shaped depression 82. A metallic semi-finished sealing element 87 is placed in hollow space 85. Die-shaped attachment 81 and matrix-shaped depression 82 are dimensioned so that an annular space 89 is formed between the opposite annular surfaces of ceramic molded components 20, 27. Another semi-finished sealing element 91, for example, in the form of a disk-shaped metallic foil, is placed in annular gap 89, for example. When pressed using pressing die 74, the metallic semi-finished sealing element 87 and the additional semi-finished sealing element 91 are hot-formed. Semi-finished sealing element 87 is pressed onto sensor element 12, forming sealing element 52. At the same time, the other semi-finished sealing element 91 in annular gap 89 is deformed and forms an additional sealing element in annular gap 89.

In order to manufacture the sensor element seal of the present invention measured gas-side ceramic molded component 20 with sensor element 12 is initially placed into receptacle 71. A disk-shaped metallic semifinished sealing element surrounding sensor element 12 is placed in depression 49 formed on face 22. Connection-side ceramic molded component 27 is then placed on the semi-finished sealing element 87 with connection-side end section 14 of sensor element 12 projecting through bushing 30. In this arrangement, a pressing force of 600 kg-force (kilogram-force), for example, is applied to connection-side ceramic molded component 27 using pressing die 74. Previously, however, the semifinished sealing element 87 is heated using a heating device mounted in matrix 70, for example, to a temperature ensuring hot-forming of the semifinished sealing element 87. In pressing, the free-flowing semi-finished sealing element 87 is pressed onto sensor element 12. The temperature set in pressing is advantageously higher than the later maximum temperature of use in the vehicle. This ensures that sealing element 52 is shrink-fitted on sensor element 12 due to its higher thermal expansion coefficient. With suitable selection of materials and additives, a diffusion welding process may take place between sealing element 52, sensor element 12, and ceramic molded components 20, 27, which ensures an absolutely gapless bond between sealing element 52, sensor element 12, and ceramic molded components 20, 27.

It is advantageous that the semifinished sealing element 87 be heated to the softening point in the device provided for performing the joining process. This can take place either prior to the joining process or simultaneously with the joining process. It is furthermore advantageous to perform the joining process in a reducing, inert, or only slightly oxidizing atmosphere.

It is also conceivable to design the sensor element sealing with two or more sealing elements axially arranged behind one another or to provide a higher number of ceramic molded components, between which one or more sealing element can be arranged.

The annular gap can also be additionally sealed by metallizing the opposite faces 22, 28 in order to achieve solid diffusion.

What is claimed is:

1. A sensor for determining an oxygen level in an exhaust gas of an internal combustion engine, comprising:

a metallic enclosure having a longitudinal bore;

a receptacle situated in the longitudinal bore of the metallic enclosure;

a sensor element seal including a hot-formable metallic sealing element hot-pressed into the receptacle; and a sensor element situated in the longitudinal bore of the metallic enclosure in a gas-tight manner via the sensor element seal.

2. The sensor according to claim 1, wherein:

the receptacle includes a measured gas-side ceramic molded component and a connection-side ceramic molded component axially arranged adjacent to the measured gas-side ceramic molded component, and a hollow space into which the sealing element is pressed is formed between the measured gas-side ceramic molded component and the connection-side ceramic molded component.

3. The sensor according to claim 2, wherein the hollow space is formed by a depression provided on at least a face of the measured gas-side ceramic molded component and a face of the connection-side ceramic molded component.

4. The sensor according to claim 1, wherein the sealing element is formed of a ductile metallic body.

5. The sensor according to claim 4, wherein the ductile metallic body is formed of one of copper, aluminum, palladium, nickel, silver, and an alloy of one of copper, aluminum, palladium, nickel, and silver.

6. The sensor according to claim 1, wherein the sealing element includes a metallic solder.

7. The sensor according to claim 6, wherein the metallic solder includes one of a hard solder and an active solder, each one of the hard solder and the active solder being formed of one of a Cu/Ag alloy, a Cu/Ag/Ti alloy, a Cu/Al alloy, and an Al/Si alloy.

8. The sensor according to claim 7, wherein the metallic solder includes an additive including one of graphite, boron nitride, talcum, bentonite, kaolin, $MoS_2$, glass, and a mixture of at least two of graphite, boron nitride, talcum, bentonite, kaolin, $MoS_2$, and glass.

9. A method of manufacturing a sensor, comprising the steps of:

placing a first ceramic molded component in a receptacle;

placing a second ceramic molded component in the receptacle adjacent to the first ceramic molded component;

inserting a sensor element through the first ceramic molded component and the second ceramic molded component;

placing a ductile semi-finished metal inside a space formed between the first ceramic molded component and the second ceramic molded component; and performing a hot-pressing operation on the ductile semi-finished metal placed inside the space formed between the first ceramic molded component and the second ceramic molded component.

10. The method according to claim 9, wherein the hot-pressing operation is performed at a temperature that is higher than a maximum temperature at which the sensor is used.

11. A sensor for determining an oxygen level in an exhaust gas of an internal combustion engine, comprising:

a metallic enclosure having a longitudinal bore;

a receptacle situated in the longitudinal bore of the metallic enclosure;

a sensor element seal including a hot-formable metallic sealing element pressed into the receptacle; and a sensor element situated in the longitudinal bore of the metallic enclosure in a gas-tight manner via the sensor element seal;

wherein the sealing element is formed of a ductile metallic body, a material of the ductile metallic body including an additive of one of graphite, boron nitride, talcum, bentonite, kaolin, $MoS_2$, glass, and a mixture of at least two of graphite, boron nitride, talcum, bentonite, kaolin, $MoS_2$, and glass.

12. A sensor for determining an oxygen level in an exhaust gas of an internal combustion engine, comprising:

a metallic enclosure having a longitudinal bore;

a receptacle situated in the longitudinal bore of the metallic enclosure;

a sensor element seal including a hot-formable metallic sealing element pressed into the receptacle; and a sensor element situated in the longitudinal bore of the metallic enclosure in a gas-tight manner via the sensor element seal;

wherein the sealing element is formed of a ductile metallic body, the ductile metallic body including a hot-formable composite body formed of a core having one of a single-sided surface coating and a double-sided surface coating.

13. The sensor according to claim 12, wherein:

the core is formed of one of copper, nickel, palladium, and an alloy of one of copper, nickel, and palladium; and each one of the single-sided surface coating and the double-sided surface coating is formed of one of aluminum, palladium, nickel, copper, and an alloy of one of aluminum, palladium, nickel, and copper.

* * * * *